US005726287A

United States Patent [19]

Andersson et al.

[11] Patent Number: 5,726,287
[45] Date of Patent: *Mar. 10, 1998

[54] SYNTHESIS OF CYCLIC PEPTIDES

[75] Inventors: Lars Henrik Harald Andersson, Lund; Jan-Ake Skoldback, Malmo, both of Sweden

[73] Assignee: Ferring AB, Malmo, Sweden

[*] Notice: The term of this patent shall not extend beyond the expiration date of Pat. No. 5,500,413.

[21] Appl. No.: 670,182

[22] Filed: Jun. 20, 1996

Related U.S. Application Data

[62] Division of Ser. No. 423,415, Apr. 18, 1995, Pat. No. 5,596,078, which is a continuation of Ser. No. 84,849, Jun. 29, 1993, abandoned.

[51] Int. Cl.⁶ .................. C07K 1/02; C07K 1/18; C07K 7/16
[52] U.S. Cl. .................. 530/315; 530/338; 530/344
[58] Field of Search ............ 530/315, 317, 530/327, 328, 329, 331, 336, 338, 344, 345; 514/11, 14, 15, 16; 930/150, DIG. 565, DIG. 566, DIG. 567

[56] References Cited

U.S. PATENT DOCUMENTS

| | | | |
|---|---|---|---|
| 3,497,491 | 2/1970 | Zaoral et al. | 930/21 |
| 3,794,633 | 2/1974 | Kamber et al. | 530/336 |
| 3,929,758 | 12/1975 | Hughes et al. | 530/307 |
| 4,033,940 | 7/1977 | Hughes et al. | 530/307 |
| 4,093,610 | 6/1978 | Abraham et al. | 530/315 |
| 4,216,141 | 8/1980 | Rivier et al. | 530/333 |
| 4,271,068 | 6/1981 | Kamber et al. | 530/336 |
| 4,351,764 | 9/1982 | Birr | 530/336 |
| 4,487,765 | 12/1984 | de Wied | 514/15 |
| 5,066,716 | 11/1991 | Robey et al. | 530/317 |
| 5,091,365 | 2/1992 | Sandow et al. | 514/12 |
| 5,482,931 | 1/1996 | Harris et al. | 514/15 |
| 5,498,598 | 3/1996 | Harris | 514/11 |
| 5,500,413 | 3/1996 | Larsson et al. | 514/15 |
| 5,596,078 | 1/1997 | Andersson et al. | 530/315 |

FOREIGN PATENT DOCUMENTS

92/00996  1/1992  WIPO.

OTHER PUBLICATIONS

Freidinger, Titanium (III) as a Selective Reducing Agent for Nitroargingl . . . J. Org. Chem. 1978, pp. 4800–4803.

*Primary Examiner*—Jeffrey E. Russel
*Attorney, Agent, or Firm*—Hopgood, Calimafde, Kalil & Judlowe, L.L.P.

[57] ABSTRACT

A process for preparing and purifying cyclic peptides having disulfide moieties in a single processing operation which simplifies synthesis and reduces production costs, yet produces high, quality yield. Higher yields are obtained by isolating the desired cyclic compound through direct ion exchange chromatography as an integral part of the single process. The improved process is particularly useful for the preparation of vasopressin and oxytocin and their respective derivatives and analogs.

9 Claims, No Drawings

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 6 amino acids
        ( B ) TYPE: amino acid
        ( C ) TOPOLOGY: linear ( i i ) MOLECULE TYPE: peptide ( v ) FRAGMENT TYPE: internal fragment ( x i ) SEQUENCE DESCRIPTION: SEQ ID NO:1:

Tyr  Phe  Gln  Asn  Cys  Pro
        1                      5

( 2 ) INFORMATION FOR SEQ ID NO:2:

( i ) SEQUENCE CHARACTERISTICS:
        ( A ) LENGTH: 4 amino acids
        ( B ) TYPE: amino acid
        ( C ) TOPOLOGY: linear ( i i ) MOLECULE TYPE: peptide ( v ) FRAGMENT TYPE: internal fragment ( x i ) SEQUENCE DESCRIPTION: SEQ ID NO:2:

Tyr  Phe  Gln  Asn
         1

( 2 ) INFORMATION FOR SEQ ID NO:3:

( i ) SEQUENCE CHARACTERISTICS:
            ( A ) LENGTH: 9 amino acids
            ( B ) TYPE: amino acid
            ( C ) TOPOLOGY: circular ( i i ) MOLECULE TYPE: peptide ( i x ) FEATURE: Cys at position 1 linked to Cys at position
            6 by a disulfide moiety ( x i ) SEQUENCE DESCRIPTION: SEQ ID NO:3:

Cys  Tyr  Phe  Gln  Asn  Cys  Pro  Lys  Gly
         1                    5

( 2 ) INFORMATION FOR SEQ ID NO:4:

( i ) SEQUENCE CHARACTERISTICS:
            ( A ) LENGTH: 12 amino acids
            ( B ) TYPE: amino acid
            ( C ) TOPOLOGY: circular ( i i ) MOLECULE TYPE: peptide ( i x ) FEATURE: Cys at position 4 linked to Cys at position
            9 by a disulfide moiety ( x i ) SEQUENCE DESCRIPTION: SEQ ID NO:4:

Gly  Gly  Gly  Cys  Tyr  Phe  Gln  Asn  Cys  Pro  Lys  Gly
         1                    5                   1 0

( 2 ) INFORMATION FOR SEQ ID NO:5:

( i ) SEQUENCE CHARACTERISTICS:
            ( A ) LENGTH: 8 amino acids
            ( B ) TYPE: amino acid
            ( C ) TOPOLOGY: linear ( i i ) MOLECULE TYPE: peptide ( v ) FRAGMENT TYPE: internal fragment ( x i ) SEQUENCE DESCRIPTION: SEQ ID NO:5:

Phe  Ile  Gln  Asn  Cys  Pro  Xaa  Gly
         1                    5

( 2 ) INFORMATION FOR SEQ ID NO:6:

( i ) SEQUENCE CHARACTERISTICS:
            ( A ) LENGTH: 8 amino acids
            ( B ) TYPE: amino acid
            ( C ) TOPOLOGY: linear ( i i ) MOLECULE TYPE: peptide ( v ) FRAGMENT TYPE: internal fragment ( x i ) SEQUENCE DESCRIPTION: SEQ ID NO:6:

Phe  Ile  Xaa  Asn  Cys  Pro  Xaa  Gly
         1                    5

1

SYNTHESIS OF CYCLIC PEPTIDES

This is a divisional of application Ser. No. 08/423,415, filed Apr. 18, 1995, now U.S. Pat. No. 5,596,078, which is a continuation of application Ser. No. 08/084,849, filed Jun. 29, 1993, now abandoned.

FIELD OF THE INVENTION

The present invention relates to an improved method for the synthesis of peptides including cyclic peptides, peptide analogs and peptide derivatives. More particularly, the present invention relates to a simplified, single-step preparation and purification of cyclic peptide compounds by oxidative cyclization of cysteine or cysteine-derived sulfhydryl groups to form the disulfide moiety.

BACKGROUND

A considerable number of known, naturally occurring small and medium-sized cyclic peptides as well as some of their artificial derivatives and analogs (in the context of the present application the term "peptide" also comprises peptide derivatives and analogs containing at least one peptide linkage) possessing desirable pharmacological properties have been synthesized up to now. However, wider medical use is often hampered by the relative complexity of their synthesis and purification. Therefore, improved methods for making these compounds are desirable.

An example for these compounds is the vasopressin analog desmopressin, a valuable medicine for the management of such ailments as diabetes insipidus and nocturnal enuresis.

In terms of peptide synthetic methodology, two major synthetic techniques dominate current practice. These are synthesis in solution (homogeneous phase) and synthesis on solid phase. In both, the desired peptide compound is created by the step-wise addition of amino acid moieties to a growing peptide chain. Larger peptide fragments can be coupled at various stages in the synthesis when working in homogeneous solution. However, a problem exists in the art for the preparation of cyclic peptide compounds based on disulfide links because separate operations are required before purifying the end product, which increases expense and may effect final product quality and quantity.

Oxidative cyclization of protected or non-protected sulfydryl groups with formation of disulfide structures usually is carried out as the final synthetic step, the reason being, inter alia, the substantial thermal and chemical lability of the disulfide linkage. An example of such a process is found in U.S. Pat. No. 4,271,068, "Process for the Manufacture of Cystine Containing Peptides" (the contents of which are incorporated by reference). This oxidation of open-chain peptides containing free and/or certain types of protected sulfhydryl groups with iodine in, e.g., methanol or acetic acid is further explained in the *CRC Handbook of Neurohypophyseal Hormone Analogs*, Vol. 1, Part 1; Jost, K., et al. Eds., CRC Press, Boca Raton, Fla. 1987, p. 31 and Table 2.

Iodine, however, is not without drawbacks as a cyclization agent (see Sieber, P., et al., 1980, Helv. Chim. Acta, 63:2358–2363; Cavalier, F., et al., 1989, Bull. Soc. Chim. France, p.788, and literature cited therein). For instance, tyrosine moieties present in peptide substrates are at risk of being iodinated, making the balance between full conversion of starting materials and minimizing side reactions a delicate one, which, in turn, impacts product purity.

The purity of a peptide has several aspects. One is purity on an active-compound concentration scale. This is represented by the relative content of the pharmacologically active compound in the final product which should be as high as possible. Another aspect is the degree of absence of pharmacologically active impurities which, though present in trace amounts only, may disturb or even render useless the beneficial action of the peptide when used as a therapeutic. In a pharmacological context both aspects have to be considered.

As a rule, purification becomes increasingly difficult with larger peptide molecules. In homogeneous phase synthesis (which is the current method of choice for industrial production of larger amounts of peptides) repeated purification required between individual steps provides a purer product but low yield. Thus, improvements in yield and purification techniques at the terminal stages of synthesis are needed.

A variety of methods, most often in combination, have been used to purify cyclic small and medium size peptides obtained by oxidative cyclization with ferricyanide, i.e. ion exchange chromatography on a weakly acidic cation exchange chromatography resin (L. Juliano, et al., 1990, *Proceedings of the Eleventh American Peptide Symposium*, J. E. Rivier and G. R. Marshall, Eds., p. 955; Escom, Leiden, NL).

Another complicating factor in known synthesis routes is the possibility of interaction between the desired cyclic disulfide and inorganic sulfur compounds used for reducing excess iodine at the end of the reaction, such as sodium dithionite or sodium thiosulfate. Such reducing sulfur-containing compounds may interact with the disulfide linkage which is sensitive to nucleophilic attack in general.

OBJECTS OF THE PRESENT INVENTION

It is an object of the present invention to provide a single step method of preparing small and medium-size, high-purity peptides containing a disulfide moiety.

It is another object of the present invention to provide a method of preparing, in a single step, select high purity vasopressin and vasopressin analogs which exhibit exceptional pharmacokinetic activity without impurities related adverse side effects.

Another object of the present invention to provide a one step method of preparig high purity oxytocin, oxytocin analogs and other related peptide compounds.

It is also an object of the present invention to provide a cyclic peptide compound, including the peptide analog desmopressin, at a relatively high purity in terms of both desired activity and reduced active impurities.

It is an additional object of the present invention to provide a method for treating diabetes insipidus and nocturnal enduresis by admistering to a patient a pharmacologically effective amount of high purity desmopressin.

SUMMARY OF THE INVENTION

The above and other objects of the present invention are provided in a specifically delineated process for forming and purifying cyclic peptide compounds in a single process step.

The present process is characterized by the elimination of separate operations to scavenge excess iodine used to form the disulfide moiety. The excess iodine is left in the solution submitted to ion exchange chromatography, enhancing yield and reducing impurities that would otherwise appear via conventional processing.

It has, thus, been surprisingly found that at the end of the oxidative cyclization reaction, excess steps (such as the removal of excess iodine by addition of reducing agents like sodium thiosulfate or dithionite and isolation of crude cyclic peptides prior to purification by ion exchange) are avoided with the present method. As explained above and shown in the following examples, the extra step of isolating intermediates or products prior to purification, reduces yield. The methodical simplification according to the present invention avoids such extra isolation processes and increases product yield without loss in purity.

The present process is a single-step method of preparing and purifiying a cyclic peptide compound containing a disulfide moiety, comprising:

a) forming a first solution by adding to a protic solvent at neutral or slightly acidic conditions, a non-cyclic peptide containing at least two reactive, protected or non-protected sulfhydryl groups;

b) forming a second solution of iodine dissolved in a protic solvent;

c) introducing the second solution containing iodine to the first solution containing the non-cyclic peptide such that the amount of iodine present in the resulting mixture is at least about stoichiometric with respect to the sulfhydryl groups;

d) supporting a disulfide moiety formation reaction until substantial amounts of said cyclic peptide compound are formed;

e) adding the cyclic peptide compound containing solution of (d) to a separation column containing cation exchange resin equilibrated with acid; and f) eluting and isolating said cyclic peptide compound.

In the above-described method, the non-cyclic peptide in the first solution (a), can have at least two sulfhydryl groups, each of which may, independently of the other, be protected or non-protected. The protonated form of this non-cyclic peptide should have an acidity constant (pK$_a$) of approximately 7.5 or higher.

According to the preferred embodiment of the invention, the straight-chain peptide used is:

β-mercapto-propionyl-Tyr-Phe-Gln-Asn-Cys-Pro-D-Arg-Gly-NH$_2$
(SEQ ID NO:1) or a derivative thereof, in which at least one of the sulfhydryl groups is protected by a protecting group which, at about ambient temperature, is unstable at a pH lower than 7 and/or in the presence of iodine. Also preferred as a straight-chain peptide is:

β-acetamido-methylmercapto-propionyl-Tyr-Phe-Gln-Asn-Cys-(S-acetamido-methyl)-Pro-D-Arg-Gly-NH$_2$ (SEQ ID NO: 2).

Preferred solvents for the second solution (b) include methanol, ethanol, acetic acid and their mixtures, including aqueous mixtures thereof.

In the method described above, the disulfide moiety formation reaction (d) should not be allowed to substantially exceed 50° C.

At about ambient temperature the cation exchange resin (e) should be substantially stable when in contact with the iodine dissolved in the protic solvents. Preferred resins are based on cross-linked agarose substituted with methylsulfonyl groups, such as S-SEPHAROSE® FF (fast flow).

It is preferred to elute (f) the cyclic peptide compound with an aqueous buffered solution, particularly with a buffered solution comprising ammonium acetate/acetic acid. The protonated form of the resulting cyclic peptide compound should have a pK$_a$ of approximately 7.5 or higher; preferably pK$_a$ 10 or higher; and most preferred is a pK$_a$ of 12 or higher.

Protonated peptides contemplated, with pK$_a$-values greater than about 12, include compounds comprising the structural element:

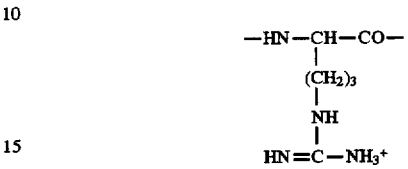

such as, protonated desmopressin (pK$_a$ ~12.5). Protonated peptides with pK$_a$-values greater than about 10 include compounds such as comprising the following structural element:

where n=3 or 4, for example, lysylvasopressin (pK$_a$ ~10.5), having the following structure:

(SEQ ID NO:3)

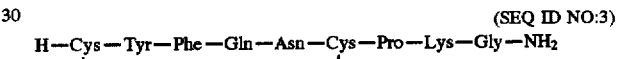

and triglycylvasopressin (pK$_a$ ~10.5) having the following structure:

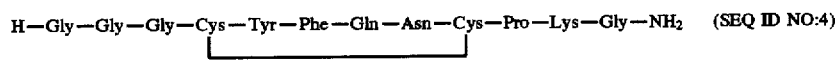 (SEQ ID NO:4)

Contemplated protonated peptides with an acidity constant pK$_a$ of about 7.5 or higher include compounds comprising the following structural element:

for example, protonated oxytocin (pK$_a$ ~7.7), and the respective protonated form of:

(SEQ ID NO:5)

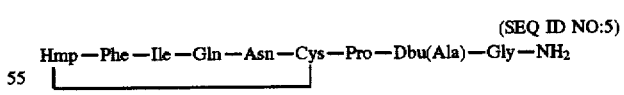

and (SEQ ID NO:6)

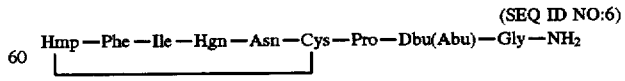

where Hmp denotes R,S-2-hydroxy-3-mercaptopropionic acid, Hgn denotes homoglutamine, Dbu denotes 2,4-diaminobutyric acid, Abu denotes 2-aminobutyric acid and Dbu(Abu) denotes:

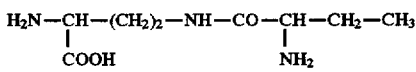

In the above-described method, the cyclic peptide compound is isolated (f) by lyophilization, particularly when using a buffer comprising compounds having measurable vapour pressure at room temperature. It is particularly advantageous to use a buffering system for lyophilization exclusively consisting of such compounds. Especially useful is a buffer comprising ammonium acetate and acetic acid or other low molecular weight fatty acids and their ammonium salts.

DETAILED DESCRIPTION

Described below is the preparation of cyclic peptides according to the present one-step synthesis and purification method, including the preferred embodiments of the invention, such as vasopressin and derivatives or analogs of vasopressin, particularly desmopressin (DDAVP). Without limiting the invention thereto, the method according of the invention will be explained in greater detail by means of the following examples.

Example 1

Preparation of Desmopressin (DDAVP) from β-p-methoxybenzylmercaptopropionyl-Tyr(2-bromobenzyloxycarbonyl)-Phe-Gln-Asn-Cys(S-p-methoxybenzyl)-Pro-D-Arg(tosyl)-Gly-NH-resin (I)

The immobilized open-chain nonapeptide derivative I was prepared by the Merrifield synthesis with the appropriate N-tert.-butyloxycarbonyl-protected (Boc) amino acids and with MBHA (4-methyl benzhydrylamine) resin (Novabiochem, Läufelingen, CH), in a way similar to that described by Krchnak V. and Zaoral, M., 1979, Coll. Czech. Chem. Comm., 44:1173–1178, except that the thiol groups were protected by p-methoxybenzyl and the phenolic hydroxyl group in tyrosine by 2-bromobenzyloxycarbonyl. Boc-Cys(p-methoxybenzyl)-OH and Boc-Tyr(2-bromo-benzyloxycarbonyl)-OH were obtained from Novabiochem and other commercial sources; β-(p-methoxybenzyl)mercapto-propionic acid was synthesized in analogy to the synthesis of S-benzyl-cysteine; cf. Acta Chem. Scand 13, 383 (1959).

The immobilized nonapeptide (I) was released by treatment of 2 g resin with a mixture of 10 ml HF, 1.0 ml of anisole and 1.0 ml of ethyl methyl sulfide and the crude deprotected nonapeptide derivative β-mercapto-propionyl-Tyr-Phe-Gln-Asn-Cys-Pro-D-Arg-Gly-NH$_2$ (II) (SEQ ID NO:1) was dissolved in 24 ml 10% HOAc/H$_2$O. 1 ml of this solution was diluted with 10% HOAc/H$_2$O to a final volume of 53 ml. To this solution was added dropwise with stirring and at ambient temperature 426 μl of a 0.1M solution of I$_2$ in 95% ethanol over a period of 90 min. Stirring was continued overnight and the slightly yellow solution (A) was divided into two equal parts.

One-Step Procedure. One half of solution (A) above was loaded on a column packed with S-SEPHAROSE® FF cross-linked agarose cation exchanger (Pharmacia) equilibrated with 5% AcOH and eluted with 0.08M HOAc/NH$_4$OAc buffer, pH 4.1. Elution was monitored at 280 nm and each fraction (2.5 ml) assayed by HPLC. Fractions containing pure DDAVP were pooled and lyophilized. White fluffy powder; yield 18 mg (76%), DDAVP-content 94.5% by HPLC.

Two-Step Procedure. The other half of solution (A) was cooled in an ice bath and decolorized by titration with 1M aqueous sodium dithionite. The resulting solution was passed through a column packed with 2 g of LICROPREP® RP-18 (C$_{18}$-reversed phase column; Merck, Darmstadt) and prewashed with H$_2$O. After removing salts by washing with 30 ml H$_2$O DDAVP was eluted with 15 ml of EtOH/HOAc/H$_2$O (85:5:15, v/v). 15 ml H$_2$O was added. EtOH evaporated under vacuum and the resulting solution purified on the Sepharose FF cation exchanger as described above. White fluffy powder, 17.5 mg (74%; purity 94% by HPLC).

Comparison of the one-step procedure according to the invention with the two-step procedure shows that the former provides the product in higher yield, shorter time and essentially the same purity. The thus obtained product may be further purified by, e.g., gel filtration, reversed-phase chromatography, and the like.

Example 2

Preparation of Desmopressin (DDAVP) from β-acetamidomethylmercaptopropionyl-Tyr(t-butyl)-Phe-Gln(4-methyltrityl)-Asn(4-methyltrityl)-Cys(S-acetamidomethyl)-Pro-D-Arg(2,2,5,7,8-pentamethylchroman-6-sulfonyl)-Gly-NH-resin (III)

The immobilized open-chain nonapeptide derivative III was prepared by conventional solid phase technique using Fmoc-(fluorenylmethyloxycarbonyl; cf. J. Chem. Soc. Perkin I 1981, 536; 538) and t-butyl-protected amino acids obtainable from commercial sources. The immobilized compound (III) was hydrolytically cleaved from the resin TENTAGEL® S-RAM (Rapp Polymere, Tübingen, Germany) and the protecting groups partially removed by treatment with a mixture of 19 ml TFA, 0.5 ml anisole and 0.5 ml of ethane dithiol at ambient temperature. The resin was removed by filtration, the filtrate evaporated and the peptide triturated with diethyl ether. The crude peptide derivative β-acetamido-metylmercaptopropionyl-Tyr-Phe-Gln-Asn-Cys(S-acetamidomethyl)-Pro-D-Arg-Gly-NH$_2$ (IV) (SEQ ID NO:2) was obtained as a white powder by filtration. Yield 251 mg (94%; FAB-MS (M+H)$^+$=1212).

Compound IV (53 mg) was dissolved in 53 ml 10% (v/v) aqueous acetic acid. During 90 min 0.0426 mmol of iodine in 426 μl ethanol was added dropwise to the peptide solution while stirring and temperature being kept at 20° C. Stirring was continued overnight. Solution (B) with a yellowish tinge was divided in two equal volumes.

One-Step Procedure. By following the procedure in Example 1, one half of solution (B) was loaded on S-SEPHAROSE® FF cation exchange resin and purified as described above. Fractions containing pure DDAVP were pooled and lyophilized. White fluffy powder, yield 15.1 mg (64%), DDAVP-content 94.5% (HPLC).

Two-Step Procedure. The other half of solution (B) was treated as described in the corresponding part of Example 1. Yield of DDAVP 12 mg (51%), DDAVP-content 94.0% (HPLC).

Comparison of the one-step procedure according to the invention with the two-step procedure shows that the former again provided the product in higher yield, shorter time and essentially the same purity.

Example 3

Preparation of Desmopressin (DDAVP) from β-tritylmercaptopropionyl-Tyr(t-butyl)-Phe-Gln(4-methyltrityl)-Asn(4-methyltrityl)-Cys(S-trityl)-Pro-D-Arg(2,2,5,7,8-pentamethylchroman-6-sulfonyl)-Gly-NH-resin (V)

A route corresponding to that described in Example 2 was followed, except for trityl being used as S-protecting group.

Compound V was decoupled by treatment with trifluoroacetic acid/scavenger (19 ml TFA, 0.5 ml anisole, 0.5 ml ethane dithiol). After evaporation, trituration and filtration of the peptide, the resulting crude β-mercaptopropionyl-Tyr-Phe-Gln-Asn-Cys-Pro-D-Arg-Gly-NH$_2$ (VI) (SEQ ID NO:1) was dissolved in 274 ml 10% HOAc/H$_2$O. 53 ml of this solution was oxidized with iodine under the conditions described in Example 2. The solution containing the reaction products was again divided into parts of equal volume which were subjected to the one-step and two-step I$_2$-oxidation/ purification procedure, respectively.

One-Step Procedure. DDAVP was obtained as a white fluffy powder. Yield 17.0 mg (72.1%), purity 92.3% (HPLC).

Two-Step Procedure. DDAVP yield 16.3 mg (69.1%), purity 92.1% (HPLC).

Example 4

Tentative Preparation of Desmopressin (DDAVP) from β-mercaptopropionyl-Tyr-Phe-Gln-Asn-Cys-Pro-D-Arg-Gly-NH$_2$ (VI) (SEQ ID NO:1) Obtained by Homogeneous Phase Synthesis A solution of crude Compound VI obtained by the method of Zaoral, et al. (Swedish Patent No. 353 530) was oxidised with iodine 10% aqueous AcOH as described in Example 2. The resulting solution containing iodine was chromatographed on S SEPHAROSE® FF cation exchange resin as described above. However, the isolation of pure DDAVP was not possible by the one-step procedure due to the high sodium ion content of the reaction mixture. This high sodium ion concentration is attributed to the deprotection step using Na/NH$_3$.

Example 5

Preparation of 1-(3-mercaptopropionic acid)-2-[3-(p-ethoxyphenyl)-D-alanine]-4-L-threonine-8-L-ornithineoxytocin (Atosiban, IX) from β-acetamidomethyl-mercaptopropionyl-D-Tyr(Et)-Ile-Thr(tBu)-Asn-Cys-(S-acetamidomethyl)-Pro-Orn(Boc)-Gly-NH-resin (VII)

The immobilized open-chain nonapeptide derivative VII was prepared by conventional solid phase technique in analogy to the synthesis of desmopressin (DDAVP; Example 2), using Fmoc (fluorenylmethyloxycarbonyl; cf. J. Chem. Soc. Perkin I 1981 536, 538) and t-butyl-protected amino acids obtainable from commercial sources, except for Fmoc-D-Tyr(Et)OH which was prepared by Fmoc protecting (Biopolymers, 1983, 22:2157–2162) of H-D-Tyr(Et)OH (Bachem AG, CH).

The immobilized compound VII was cleaved from resin and the protecting groups partially removed by treatment with a mixture of TFA/water (95:5) for 2 h at room temperature. The resulting β-acetamido-methyl-mercaptopropionyl-D-Tyr(Et)-Ile-Thr-Asn-Cys(S-acetamidomethyl)-Pro-Orn-Gly-NH$_2$ (VIII) was triturated with ether, collected by filtration, washed with ether and obtained in form of white powder. Overall yield 70%. Characterized by FAB-MS; (M+M$^+$=994). 48.3 mg VIII was oxidized with iodine by the method described above and the resulting solution divided into two equal parts of which one was purified by the one-step method. Yield of atosiban (IX) 12 mg (57%), purity 90% HPLC).

While the invention has been fully disclosed hereinabove, it is within the skill of those in the art to modify those methods, reagents and reaction conditions described herein to obtain similar results. Such modifications are within the spirit and scope of the present disclosure. For instance, the foregoing methods may be applied to oxytocin and its analogs with the expectation that similar advantageous results will occur in terms of both yield and purity.

---

We claim:

1. A method for preparing and purifying cyclic peptide compounds containing a disulfide moiety, comprising:
   a) forming a first solution by adding to a protic solvent at neutral or acidic pH, a non-cyclic peptide containing at least two reactive, protected or non-protected sulfhydryl groups;
   b) forming a second solution of iodine dissolved in a protic solvent;
   c) introducing said second solution containing iodine to said first solution containing said non-cyclic peptide such that the amount of iodine present in the resulting mixture is at least about stoichiometric with respect to the sulfhydryl groups;
   d) allowing the mixture resulting from step (c) sufficient time for disulfide moiety formation and conversion of said non-cyclic peptide to said cyclic peptide compound;
   e) adding the mixture from step (d) containing said cyclic peptide compound directly to a separation column containing cation exchange resin;
   f) eluting said cyclic peptide compound; and
   g) isolating said cyclic peptide compound.

2. The method of claim 1, wherein said non-cyclic peptide in its protonated form has an acidity constant ($pK_a$) of approximately 7.5 or higher.

3. The method of claim 1, wherein said non-cyclic peptide in its protonated form has an acidity constant ($pK_a$) of approximately 10 or higher.

4. The method of claim 1, wherein said non-cyclic peptide in its protonated form has an acidity constant ($pK_a$) of approximately 12 or higher.

5. The method of claim 1, wherein said non-cyclic peptide is:

β-acetamido-methylmercapto-propionyl-Tyr-Phe-Gln-Asn-Cys-(S-acetamido-methyl)-Pro-D-Arg-Gly-NH$_2$(SEQ ID NO: 2).

6. The method of claim 1, wherein said disulfide moiety formation reaction (d) is carried out below approximately 50° C.

7. The method of claim 1, wherein said second solution (b) contains a stoichiometric excess of iodine.

8. The method of claim 1, wherein said cyclic peptide compound is eluted (f) with an aqueous buffer solution selected from the group consisting of ammonium acetate, acetic acid, and combinations of ammonium acetate and acetic acid.

9. The method of claim 1, wherein said isolated cyclic peptide compound is selected from the group consisting of vasopressin and oxytocin.

* * * * *